United States Patent [19]

Wätjen et al.

[11] Patent Number: 4,780,539
[45] Date of Patent: Oct. 25, 1988

[54] 3-SUBSTITUTED-4,5-DIHYDRO-5-OXO IMIDAZOQUINAZOLINES, THEIR PREPARATION, AND THEIR USE IN TREATING BENZODIAZEPIN RECEPTOR-RELATED AILMENTS

[75] Inventors: Frank Wätjen; Mogens Engelstoft, both of Vaerloese, Denmark

[73] Assignee: A/S Ferrosan, Søborg, Denmark

[21] Appl. No.: 143,364

[22] Filed: Jan. 12, 1988

Related U.S. Application Data

[60] Division of Ser. No. 912,775, Sep. 26, 1986, Pat. No. 4,771,051, which is a continuation-in-part of Ser. No. 879,198, Jun. 26, 1986, abandoned, which is a division of Ser. No. 816,731, Jan. 6, 1986, Pat. No. 4,622,321.

[30] Foreign Application Priority Data

Oct. 17, 1985 [DK] Denmark .................. 4768/85
Oct. 17, 1985 [DK] Denmark .................. 4769/85

[51] Int. Cl.$^4$ ........................... C07D 271/06
[52] U.S. Cl. ................................... 548/131
[58] Field of Search ........................ 548/131

[56] References Cited

U.S. PATENT DOCUMENTS 4,622,321 11/1986 Watjen ................ 514/210
4,670,433 6/1987 Watjen ................ 514/210

FOREIGN PATENT DOCUMENTS 0150040 7/1985 European Pat. Off. ........... 548/131

Primary Examiner—Robert Gerstl
Attorney, Agent, or Firm—Gordon W. Hueschen

[57] ABSTRACT

New heterocyclic compounds having the general formula

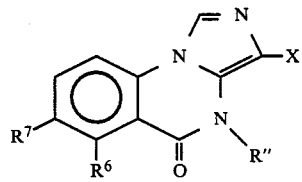

wherein
X is

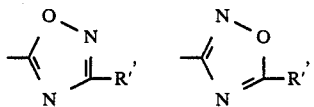

or $CO_2R'$ wherein $R'$ is $C_{1-6}$-alkyl, $C_{3-7}$-cycloalkyl, or $C_{3-7}$-cycloalkymethyl,
$R^6$ and $R^7$ independently are hydrogen, halogen, alkoxy, or trifluoromethyl, and
$R''$ hydrogen, $C_{1-6}$-alkyl, or $C_{3-7}$-cycloalkyl.

The compounds are useful in psychopharmaceutical preparations as anticonvulsants, anxiolytics, hypnotics, and nootropics.

3 Claims, No Drawings

3-SUBSTITUTED-4,5-DIHYDRO-5-OXO IMIDAZOQUINAZOLINES, THEIR PREPARATION, AND THEIR USE IN TREATING BENZODIAZEPIN RECEPTOR-RELATED AILMENTS

This application is a division of application Ser. No. 912,775, filed Sept. 26, 1986, now U.S. Pat. No. 4,771,051, which in turn is a continuation-in-part of our prior-filed copending application Ser. No. 879,198, filed June 26, 1986, now abandoned, which in turn is a division of our prior-filed copending application Ser. No. 816,731, filed Jan. 6, 1986, now U.S. Pat. No. 4,622,321, Heterocyclic Compounds and Their Preparation and Use. The present invention relates to therapeutically active heterocyclic compounds, a method of preparing the same, pharmaceutical compositions comprising the compounds, and to methods of treating therewith. The novel compounds are useful in psychopharmaceutical applications, e.g., in the treatment of central nervous system ailments, for example, as anticonvulsants or anxiolytics.

It is well known (Squires, R. F. and Braestrup, C. in Nature (London) 266 (1977) 732–734) that specific sites in the central nervous systems of vertebrates exhibit a high specific affinity for binding 1,4- and 1,5-benzodiazepines. These sites are called benzodiazepine receptors.

It has now been found that members of a novel group of quinazoline compounds have strong affinity for the benzodiazepine receptors which make them useful in psychopharmaceutical preparations.

Accordingly, it is an object of the invention to provide such novel quinazoline compounds.

The quinazoline compounds of the invention are heterocyclic compounds having the general formula I

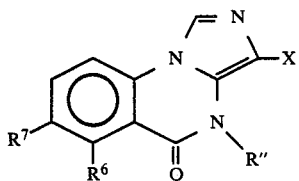

wherein
X is

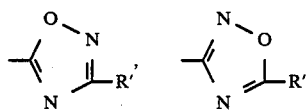

or $CO_2R'$ wherein $R'$ is $C_{1-6}$-alkyl, $C_{3-7}$-cycloalkyl, or $C_{3-7}$-cycloalkylmethyl, $R^6$ and $R^7$ independently are hydrogen, halogen, alkoxy, or trifluoromethyl, and R" is hydrogen, $C_{1-6}$-alkyl, or $C_{3-7}$-cycloalkyl.

The pharmaceutical properties of the compounds of the invention can be illustrated by determining their capability for displacing radioactivity labelled flunitrazepam from benzodiazepine receptors.

The displacement activity of the compounds of the invention may be found by determining the $ED_{50}$ value. The $ED_{50}$ value represents the dose (mg/kg) of a test substance which causes the specific binding of flunitrazepam to benzodiazepine reoeptors in a living brain to be reduced to 50% of the control value.

Such an in vivo test is carried out as follow:

Principle. Twenty minutes after a dose of $^3H$-flunitrazepam ($^3H$-FNM) (200μ Ci/kg, i.v.) the amount of specific $^3H$-FNM binding to brain benzodiazepine receptors has reached its maximal value. This specific binding of $^3H$-FNM can be partly or completely prevented by simultaneous or prior administration of pharmacologically active benzodiazepines and by some benzodiazepine-like agents (Chang and Snyder, Eur.J. Pharmacol. 48, 212–218 (1978)).

Test procedure. Suspensions of test substances (2 mg/ml) are prepared in 5% Duphasol-X (TM Duphar, castor oil-ethylene oxide derivative for emulsifying and solubilizing oil and other water-insoluble substances) by sonification for 10 min using a Branson B15 microtip ultrasonifier (setting 7). Groups of three mice (female, NMR,18–22 grams) are injected with the test substance at 100 mg/kg intraperitoneally. Fifteen minutes after test substance administration the mice are challenged with 4μ Ci intravenously of $^3H$-FNM (70–90 Ci/mole) in 200 μphysiological saline. Twenty minutes after $^3H$-FNM administration mice are sacrificed by decapitation, the forebrains rapidly excised (within 30 sec) and homogenized in 12 ml of icecold 25 mM $KH_2PO_4$, 7.1, using an Ultra-Turrax homogenizer fitted with an N 10 shaft. Two aliquots of 1 ml are immediately filtered through Whatman GF/C glassfibre filters and washed with 2×5 ml of the above mentioned buffer. The amounts of radioactivity on the filters are determined by conventional scintillation counting. One group of untreated mice serves as control. One to three mice are injected with 25 g/kg clonazepam i.p. 30 minutes before $^3H$-FNM to determine the amount of non-specific $^3H$-FNM binding, which should be between 8–15% of total binding. When doses of 100 mg/kg inhibit more than 50% of specific $^3H$-flunitrazepam binding; test substances are administered in doses, which are factors of 3.16 times lower than 100 mg/kg. The $ED_{50}$ for a test substance is defined as that dose which inhibits 50% of specific $^3H$-FNM binding. Specific binding is the amount of binding in controls minus the amount binding in clonazepam-treated mice.

Results. The $ED_{50}$ value is determined from dose response curves. If only one dose of test substance is administered the $ED_{50}$ value is calculated as follows, provided that the inhibition of specific binding is within the range of 25–75%:

$$ED_{50} = (\text{administered dose}) \times \frac{1}{\left(\frac{C_o}{C_x} - 1\right)} \text{ mg/kg}$$

where $C_o$ is specific binding in controls and $c_x$ is specific binding in mice treated with test substance.

Test results obtained by testing some compounds of the invention will appear from the follwing table I.

TABLE 1

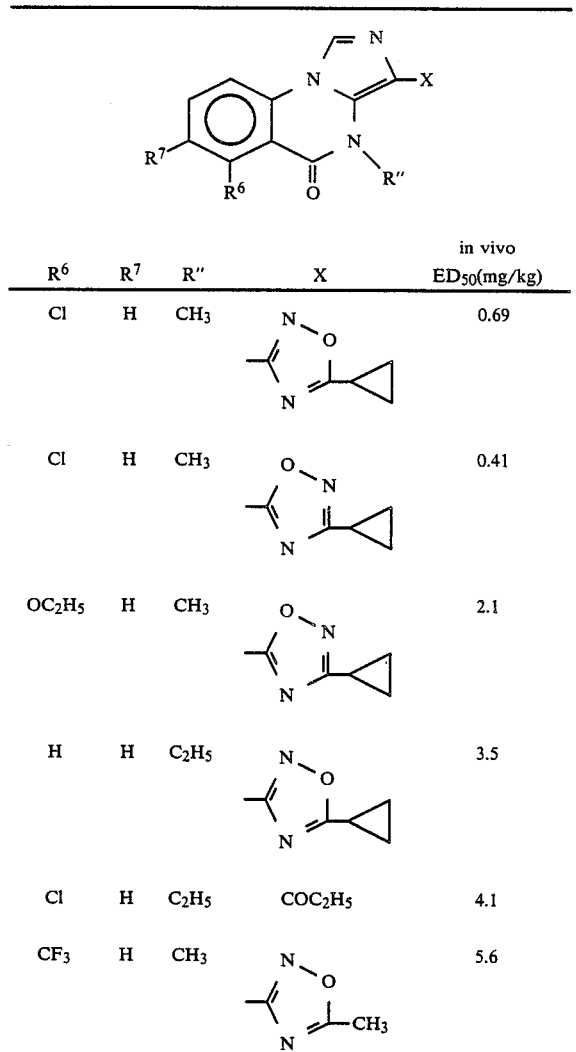

| $R^6$ | $R^7$ | $R''$ | X | in vivo $ED_{50}$(mg/kg) |
|---|---|---|---|---|
| Cl | H | $CH_3$ | | 0.69 |
| Cl | H | $CH_3$ | | 0.41 |
| $OC_2H_5$ | H | $CH_3$ | | 2.1 |
| H | H | $C_2H_5$ | | 3.5 |
| Cl | H | $C_2H_5$ | $COC_2H_5$ | 4.1 |
| $CF_3$ | H | $CH_3$ | | 5.6 |

The invention also relates to a method of preparing the above mentioned compounds. This method comprises:

(a) reacting a compound of formula II

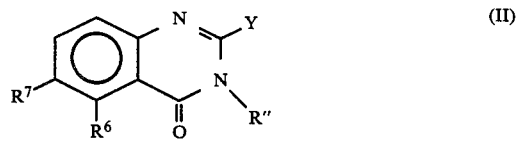

(II)

wherein $R''$, $R^6$ and $R^7$ have the meanings set forth above and wherein Y is a leaving group, with a compound having the formula III $$CN-CH_2-X \qquad (III)$$

wherein X has the meaning set forth above, to form a compound of the invention, or (b) reacting a reactive derivative of a compound having the general formula IV

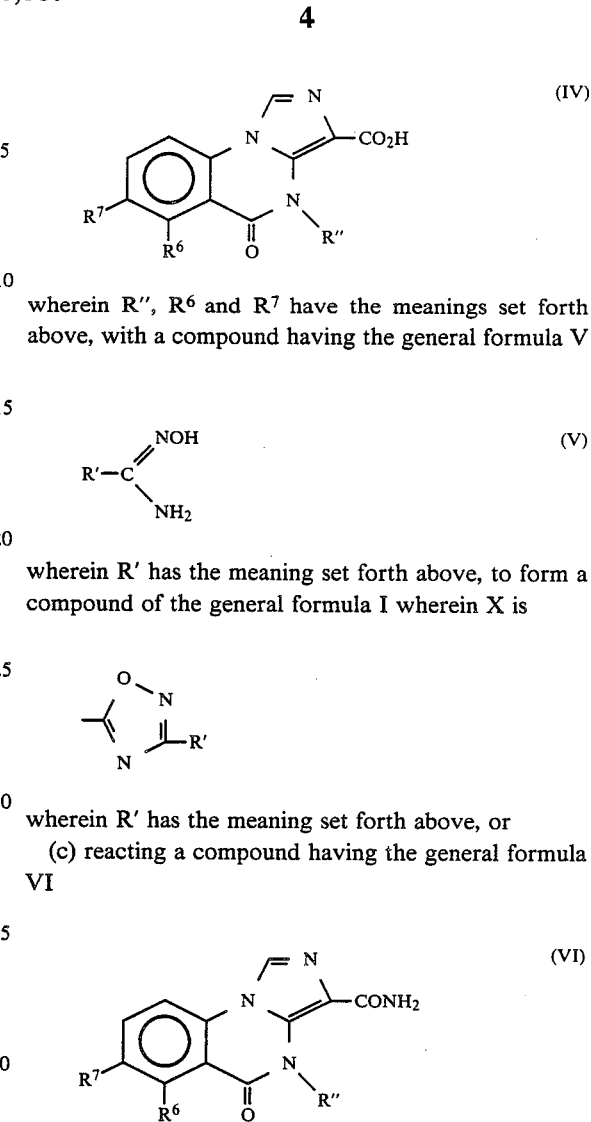

(IV)

wherein $R''$, $R^6$ and $R^7$ have the meanings set forth above, with a compound having the general formula V

(V)

wherein $R'$ has the meaning set forth above, to form a compound of the general formula I wherein X is

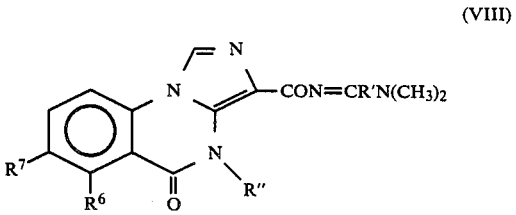

wherein $R'$ has the meaning set forth above, or (c) reacting a compound having the general formula VI (VI)

wherein $R''$, $R^6$ and $R^7$ have the meanings set forth above, with a compound having the general formula VI $$R'-C(OCH_3)_2N(CH_3)_2 \qquad (VII)$$

wherein $R'$ has the meaning set forth above, to form a compound having the general formula VIII (VIII)

wherein $R'$, $R''$, $R^6$ and $R^7$ have the meanings set forth above, and reacting the compound having the formula (VIII) with $NH_2OH$ or another aminating agent to form a compound having the generic formula I, wherein X is

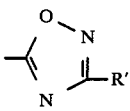

wherein R' has the meaning defined above, or (d) reacting a compound having the general formula IX

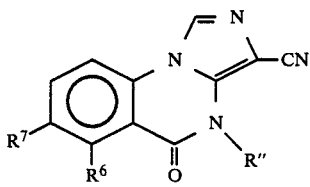

wherein R", R⁶ amd R⁷ have the meanings set forth above, with NH₂OH to form a compound having the general formula X

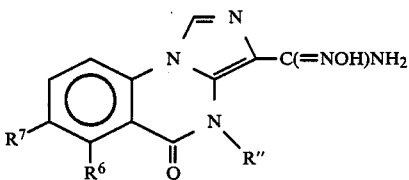

wherein R", R⁶ and R⁷ have the meanings set forth above, and reacting the compound having the formla (X) with R'—COCl, wherein R' has the meaning set forth above, to form a compound of formula I, wherein X is

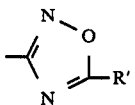

wherein R' has the meaning set forth above.

The leaving group, Y, may be any suitable leaving group and, for example, those disclosed in U.S. Pat. Nos. 4,031,079 or 4,359,420, for example, halogen, alkylthio, e.g., methylthio, aralkylthio, N-nitrosoalkylamino, alkoxy, mercapto, —OP(O)(OR)₂ wherein R is lower-alkyl or —OP(O)(NR'R") wherein R' and R" each represents lower-alkyl or phenyl, or together with the nitrogen atom to which they are attached represent a heterocyclic radical such as morpholino, pyrrolidino, piperidino, or methylpiperazino. The reaction is preferably carried out under alkaline conditions, i.e., in the presence of a base, and among bases alkali metal, e.g., potassium or sodium, alkoxides or hydrides are preferred. The reaction is preferably conducted in the presence of an organic solvent which is nonreactive with the reactants and products of reaction under the conditions of reaction, especially an anhydrous solvent and preferably an anhydrous aprotic solvent such as dimethylformamide (DMF) or the like. The temperature range employed may be any range suitable for the reaction to proceed at a reasonable rate and without undue delay or decomposition and a range from a minus forty (−40) degrees Celsius to about room temperature is accordingly usually particularly suitable.

The starting materials may be prepared from commercially available benzene derivatives and by using well known synthetic methods and as described in Synthesis, Vol. 10, pp. 681–682.

The compounds of the invention, together with a conventional adjuvant, carrier, or diluent, and if desired in the form of a pharmaceutically-acceptable acid addition salt thereof, may be placed into the form of pharmaceutical compositions and unit dosages thereof, and in such form may be employed as solids, such as tablets or filled capsules, or liquids, such as solutions, suspensions, emulsions, elixirs, or capsules filled with the same, all for oral use, in the form of suppositories for rectal administration; or in the form of sterile injectable solutions for parenteral (including subcutaneous) use. Such pharmaceutical compositions and unit dosage forms thereof may comprise conventional ingredients in conventional proportions, with or without additional active compounds or principles, and such unit dosage forms may contain any suitable effective central nervous system ailment alleviating amount of the active ingredient commensurate with the intended daily dosage range to be employed. Tablets containing one (1) milligrams of active ingredient or, more broadly, one (1) to hundred (100) milligrams, per tablet, are accordingly suitable representative unit dosage forms.

The compounds of this invention can thus be used for the formulation of pharmaceutical preparations, e.g., for oral and parenteral administration to mammals including humans, in accordance with conventional methods of galenic pharmacy.

Conventional excipients are such pharmaceutically acceptable organic or inorganic carrier substances suitable for parenteral or oral application which do not deleteriously react with the active compound.

Examples of such carriers are water, salt solutions, alcohols, polyethylene glycols, polyhydroxyethoxylated castor oil, gelatin, lactose, amylose, magnesium stearate, talc, silicic acid, fatty acid monoglycerides and diglycerides, pentaerythritol fatty acid esters, hydroxymethylcellulose and polyvinylpyrrolidone.

The pharmaceuticol preparations can be sterilized and mixed, if desired, with auxilliary agents, such as lubricants, preservatives, stabilizers, wetting agents, emulsifiers, salt for influencing osmotic pressure, buffers and/or coloring substances and the like, which do not deleteriously react with the active compound.

For parenteral application, particularly suitable are injectable solutions or suspensions, preferably aqueous solutions with the active compound dissolved in polyhydroxylated castor oil.

Ampoules are convenient unit dosage forms.

For oral application, particularly suitable are tablets, dragees, or capsules having talc and/or a carbohydrate carrier or binder or the like, the carrier preferably being lactose and/or corn starch and/or potato starch. A syrup, elixir or like can be used when a sweetened vehicle can be employed. Generally, as to broader ranges, the compound of the invention is dispensed in unit dosage form comprising 0.1–100 mg in a pharmaceutically-acceptable carrier per unit dosage.

A typical tablet which may be prepared by conventional tabletting techniques contains:

| | |
|---|---|
| Active compound | 1.0 mg |
| Lactosum | 67.8 mg Ph. Eur. |
| Avicel ® | 31.4 mg |

| Amberlite ® IRP 88 | 1.0 mg |
| Magnesii stearas | 0.25 mg Ph. Eur. |

Due to their high degree of affinity for the benzodiazepin receptors, the compounds of the invention are extremely useful in the treatment of central nervous system ailments or disorders, when administered in an amount effective for the alleviation, amelioration. or elimination thereof. The important CNS activity of the compounds of the invention includes both anticonvulsant and anxiolytic activities along with a low toxicity, together presenting a most favorable therapeutic index. The compounds of the invention may accordingly be administered to a subject, e.g., a living animal body, including a human, in need of the same for the treatment, alleviation, amelioration, or elimination of an indication, associated with the central nervous system and the socalled benzodiazepin receptors, which requires such psychopharmaceutical treatment, e.g., especially convulsion and/or anxiety states, if desired in the form of a pharmaceutically-acceptable acid addition salt thereof (such as the hydrobromide, hydrochloride, or sulfate, in any event prepared in the usual or conventional manner, e.g., evaporation to dryness of the free base in solution together with the acid), ordinarily concurrently, simultaneously, or together with a pharmaceutically-acceptable carrier or diluent, especially and preferably in the form of a pharmaceutical composition thereof, whether by oral, rectal, or parenteral (including subcutaneous) route, in an effective psychopharmaceutical central nervous system ailment alleviating amount, e.g., an anticonvulsant and/or anxiolytic amount, and in any event an amount which is effective for the alleviation of such a central nervous system ailment due to their benzodiazepine receptor affinity. Suitable dosage ranges are 1–100 milligrams daily preferably 1–30 milligrams daily, and especially 1–10 milligrams daily, depending as usual upon the exact mode of administration, form in which administered, the indication toward which the administration is directed, the subject involved and the body weight of the subject involved, and the preference and experience of the physician or veterinarian in charge. Broader ranges for dosages of the compounds according to this invention are 0.1–100 mg/day, preferably 1–30 mg/day, when administered to patients, e.g., humans, as a drug.

The invention will now be described in further detail with reference to the following examples:

EXAMPLE 1

A. Isatoic anhydride 7.5 g of 2-amino benzoic acid hydrochloride was mixed with 10 ml of diphosgene and the mixture was stirred in 150 ml of dioxane for 40 minutes at reflux. The resulting mixture was cooled and filtered Yield: 5.7 g of title compound.

In the same manner, from the appropriate aminobenzoic acids, the following compounds were synthesized:
6-fluoroisatoic anhydride
6-chloroisatoic anhydride
6-bromoisatoic anhydride
6-trifluoromethylisatoic anhydride
5-chloroisatoic anhydride
5-fluoroisatoic anhydride

B. 1,2,3,4-tetrahydro-3-methyl-2,4-dioxo-quinazoline 6 g isatoic anhydride was stirred in 100 ml dry tetrahydrofurane(THF) and methylamine was passed through the mixture for 5 min. The resulting solution was evaporated and the residue was again dissolved in THF (100 ml) and charged with 15 ml 30% phosgene solution in toluene. The mixture was heated to reflux and additional 15 ml phosgene solution was added After 4 hours reflux the mixture was cooled and evaporated to dryness. The residue was treated with water and the crystals were collected by filtration. The yield was 3.5 g. M.p. 240.4°–240.5° C.

In the same manner, from the appropriate substituted isatoic anhydrides, the following compounds were synthesized:
3-methyl-5-chloro-2,4-dioxo-1,2,3,4-tetrahydro-quinazoline. M.p. 226°–229° C.
3-methyl-5-bromo-2,4-dioxo-1,2,3,4-tetrahydro-quinazoline. M.p. 280° C.
3-methyl-6-chloro-2,4-dioxo-1,2,3,4-tetrahydro-quinazoline.
3-methyl-6-fluoro-2,4-dioxo-1,2,3,4-tetrahydro-quinazoline.
3-methyl-5-fluoro-2,4-dioxo-1,2,3,4-tetrahydro-quinazoline.
3-methyl-5-trifluoromethyl-2,4-dioxo-1,2,3,4-tetrahydro-quinazoline.

C. 3-methyl-5-iodo-2,4-dioxo-1,2,3,4-tetrahydro-quinazoline 1.81 g of 3-methyl-5-bromo-2,4-dioxo-1,2,3,4-tetrahydro-quin- noxaline, 11.8 g of potassium iodide and 6.76 g of cuprous iodide was stirred in 40 ml of HMPA (hexamethylphosphoramide) at 150° C. under nitrogen for 7 hours. The mixture was then left at room temperature overnight. Next day 40 ml 1M hydrochloric acid, 40 ml water and 50 ml methylene chloride was added. The combined mixture was filtered and the methylene chloride phase of the filtrate was evaporated in vacuo to give 1.3 g of residue. The residue was recrystallized from acetone. Yield: 0.77 g of the title compound. M.p. >300° C.

D. 3-cyclopropyl-5-isocyanomethyl-1,2,4-oxadiazole a. 3-cyclopropyl-5-formylaminomethyl-1,2,4-oxadiazole.

A solution of ethyl formylaminomethyl-carboxylate (150 mmol) and cyclopropyl carboxamide oxime (100 mmol) in 100% EtOH (100 ml) was charged with Na (200 mg) and crushed molecular sieve (4Å) (10 g). The mixture thus obtained was stirred and heated to reflux for 8 hours. The mixture was cooled to room temperature, filtered through filter aid and the filtrate was evaporated in vacuo. The oily residue was partitionated into a $CHCl_3$ phase which was dried with $Na_2SO_4$ and evaporated.

b. 3-cyclopropyl-5-isocyanomethyl-1,2,4-oxadiazole.
A stirred solution of 3-cyclopropyl-5-formylaminomethyl1,2,4-oxadiazole (60 mmol) and triethylamine (176 mmol) in $CH_2Cl_2$ (100 ml) was charged dropwise with $POCl_3$ (60 mmol) at 0° C. The mixture was then left for 30 minutes with stirring at 0° C., whereafter a solution of $Na_2CO_3$ (60 mmol) in HO (50 ml) was added. The mixture was heated to room temperature, whereafter the organic phase was separated, dried and evaporated in vacuo. The residue was treated with ether, decanted and the solution was evaporated to give the title compound as an oil. The oil was processed without any further purification. The compound was characterized by its IR absorbtion band at 2160 cm$^{-}$.

3-ethyl-5-isocyanomethyl-1,2,4-oxadiazole was prepared from 3-ethyl-5-formylaminomethyl-1,2,4-oxadiazole in a similar manner. IR: cm$^{-1}$: 2170.

E. 5-cyclopropyl-3-isocyaomethyl-1,2,4-oxadiazole a. Formylaminomethyl-carboxamide oxime.

0.55 mmol of freshly liberated hydroxylamine dissolved in 370 ml methanol was added to 53.6 g (0.638 mmol) N-formylamino-acetonitrile. An ice bath was used to keep the temperature below 20° C. during addition. The solution was allowed to stand at room temperature overnight, whereafter it was evaporated to give the title compound as pale crystals. Decomp. 104°–110° C.

b. 3-formylaminomethyl-5-cyclopropyl-1,2,4-oxadiazole

A mixture of 35 ml ethyl cyclopropylcarboxylate, 20 g formylamino-methylcarboxamide oxime, 1 g sodium and 30 g of crushed molecular sieve (4Å) was refluxed in 300 ml abs. EtOH for 8 hours whereafter a further 1 g sodium was added. The reaction mixture was filtered and the filtrate was evaporated. The dark oily residue was suspended in 300 ml CHCl$_3$, filtered and the filtrate was evaporated to give the title compound as an oil. H-NMR (60 MHz, CDCl$_3$) (ppm): 1.2 (4H, m), 2.8 (1H, m), 4.5 (2H, d, J=6Hz), 7.8 (1H, broad-NH), 8.2 (1H, s).

The following compounds were synthesized from the appropriate ethyl esters in a similar manner:

3-Formylaminomethyl-5-ethyl-1,2,4-oxadiazole. H-NMR(60 MHz, CDCl$_3$) (ppm): 1.4 (3H, t, J=8 Hz), 2.9 (2H, q, J=8Hz) 4.55 (2H, s) ,7.8 (1H, broad-NH), 8.25 (1H, s).

3-Formylaminomethyl-5-methyl-1,2,4-oxadiazole. H-NMR (60 MHz, CDCl$_3$) (ppm); 2.6 (3H, s), 4.6 (2H, d, J=3 Hz), 7.4 (1H, broad-NH), 8.25 (1H, s).

3-Formylaminomethyl-5-methoxymethyl-1,2,4-oxadiazole H-NMR (60 MHz, CDCl$_3$) (ppm): 3.5 (3H, s), 4.7 (4H, s+d, J=6 Hz), 7.8 (1H, broad-NH), 8.25 (H, s).

c. 5-Cyclopropyl-3-isocyanomethyl-1,2,4-oxadiazole

A stirred solution of 5-cyclopropyl-3-formylaminomethyl1,2,4-oxadiazole (60 mmol) and triethylamine (176 mmol) in CH$_2$Cl$_2$(100 ml) was charged dropwise with POCl$_3$ (60 mmol) at 0° C. The mixture was then left for 30 minutes with stirring at 0° C., whereafter a solution of Na$_2$CO$_3$ (60 mmol) in H$_2$O (50 ml) was added. The mixture was heated to room temperature, whereafter the organic phase was separated, dried and evaporated in vacuo. The residue was treated with ether, decanted and the solution was evaporated to give the title compound as an oil. The oil was processed without any further purification. The compound was characterized by its IR absorbtion band at 2160 cm$^{-1}$.

5-Ethyl-3-isocyanomethyl-1,2,4-oxadiazole, 5-methyl-3-isocyanomethyl-1,2,4-oxadiazole, and 5-methoxymethyl-3-isocyanomethyl-1,2,4-oxadiazole were prepared in a similar manner. All compounds were oils and were characterized by their IR stretching band at 2160 cm$^{-1}$.

F. 3-(5-ethyl-1,2,4-oxadiazol-3-yl)-4,5-dihydro-4-methyl 5-oxo-imidazo(1,5-a)quinazoline 3-methyl-1,2,3,4-tetrahydro-2,4-dioxo-quinazoline (5 mmol) was dissolved in dry dimethyl formamide DMF (20 ml) and charged with sodium hydride (6 mmol). The resulting solution was cooled under N$_2$ to −20° C., whereafter chlorodiethylphosphate (6 mmol) was added. The reaction mixture was kept under N$_2$ with stirring and was allowed to reach room temperature and was then charged with a −30° C. cold solution of 5-ethyl-3-isocyanomethyl-1,2,4-oxadiazole (6 mmol) and K-t-butylate (6 mmol) in dry DMF (15 ml). The resulting mixture was stirred at room temperature for one hour whereafter the reaction mixture was evaporated in vacuo. The residue was partitioned between ethyl acetate and 4M sodium hydroxide. The organic phase was dried and evaporated. Yield 120 mg of title compound. M.p. 199.4°–202.2° C.

In the same manner the following compounds were synthesized:

Ethyl 4,5-dihydro-4-methyl-5-oxo-imidazo(1,5-a)quinazoline-3-carboxylate. M.p. 211.4°–211.8° C. by reaction between 3-methyl-1,2,3,4-tetrahydro-2,4-dioxo-quinazoline and ethyl isocyanoacetate.

Ethyl 4,5-dihydro-4-methyl-5-oxo-6-chloro-imidazo(1,5-a)-quinazoline-3-carboxylate. M.p. 248°–254° C. by reaction between 3-methyl-5-chloro-1,2,3,4-tetrahydro-2,4-dioxo-quinazoline and ethyl isocyanoacetate.

Ethyl 4,5-dihydro-4-methyl-5-oxo-6-bromo-imidazo(1,5-a)-quinazoline-3-carboxylate. M.p. 272° C. by reaction between 3-methyl-5-bromo-1,2,3,4-tetrahydro-2,4-dioxo-quinazoline and ethyl isocyanoacetate.

3-(5-cyclopropyl-1,2,4-oxadiazol-3-yl)-4,5-dihydro-4-methyl-5-oxo-6-chloro-imidazo(1,5-a)quinazoline. M.p. 230°–240° C. (decomp.) by reaction between 3-methyl-5-chloro-1,2,3,4-tetrahydro-2,4-dioxo-quinazoline and 5-cyclopropyl-3methyl-1,2,4-oxadiazole.

3-(5-cyclopropyl-1,2,4-Oxadiazol-3-yl)-4,5-dihydro-4-methyl-5-oxo-6-bromo-imidazo(1,5-a)quinazoline. M.p. 206.6° C. by reaction between 3-methyl-5-bromo-1,2,3,4-tetrahydro-2,4-dioxo-quinazoline and 5-cyclopropyl-3-isocyanomethyl-1,2,4-oxadiazole.

3-(5-ethyl-1,2,4-oxadiazol-3-yl)-4,5-dihydro-4-methyl-5-oxo-7-chloro-imidazo(1,5-a)quinazoline. M.p. 196°–198° C. by reaction between 3-methyl-6-chloro-1,2,3,4-tetrahydro-2,4-dioxoquinazoline and 5-ethyl-3-isocyanomethyl-1,2,4-oxadiazole.

3-(5-cyclopropyl-1,2,4-oxadiazol-3-yl)-4,5-dihydro-4-methyl5-oxo-6-iodo-imidazo(1,5-a)quinazoline. M.p. 217°–220° C. by reaction between 3-methyl-5-iodo-1,2,3,4-tetrahydro-2,4-dioxo-quinazoline and 5-cyclopropyl-3-isocyanomethyl-1,2,4-oxadiazole.

Ethyl 4,5-dihydro-4-methyl-5-oxo-6-iodo-imidazo(1.5-a)- quinazoline-3-carboxylate. M.p. 266°–267° C. by 3-methyl-5-iodo-1,2,3,4-tetrahydro-2,4-dioxo-quinazoline and ethyl isocyanoacetate.

3-(5-cyclopropyl-1,2,4-oxadiazol-3yl)-4,5-dihydro-4-methyl5-oxo-imidazo(1,5-a)quinazoline. M.p. 206.7°–207.8° C. by reaction between 3-methyl-1,2,3,4-tetrahydro-2,4-dioxoquinazoline and 5-cyclopropyl-3-isocyanomethyl-1,2,4-oxadiazole.

3-(5-methyl-1,2,4-oxadiazol-3-yl)-4,5-dihydro-4-methyl-5-oxo-6-trifluoromethyl-imidazo(1,5-a)quinazoline, M.p. 251.5°–251.9° C., by reaction between 3-methyl-5-trifluoromethyl 1 2,3,4-tetrahydro-2,4-dioxoquinazoline and 5-methyl-3-isocyanomethyl-1,2,4-oxadiazole.

3-(3-cyclopropyl-1,2,4-oxadiazol-5-yl)-4,5-dihydro-4-methyl5-oxo-6-bromo-imidazo(1,5-a)quinazoline. M.p. 246°–247° C. by reaction between 3-methyl-5-bromo- 1,2,3,4-tetrahydro-2,4-dioxo-quinazoline and 3-cyclopropyl-5-isocyanomethyl-1,2,4-oxadiazole.

EXAMPLE 2

3-(5-cyclopropyl-1,2,4-oxadiazol-3-yl)-4,5-dihydro-4-methyl-5-oxo-6-ethoxy-imidazo(1,5-a)quinazoline 30 mg of sodium was dissolved in 10 ml of dry ethanol. Then 3-(5-cyclopropyl-1,2,4-oxadiazol-3-yl)-4,5-dihydro-4-methyl-5-oxo-6-chloro-imidazo(1,5-a)quinazoline (0.2 g, 0.5 mmol) was added and the resulting mixture was refluxed for 7 hours. The reaction mixture was evaporated. Glacial acetic acid and water was added to the residue whereupon the title compound was isolated by filtration. M.p. 195°–205° C.

EXAMPLE 3

A. Methoxyacetamide oxime 2.3 g of sodium in 33 ml of dry methanol was mixed with 6.55 g of hydroxylamine hydrochloride in 66 ml of dry methanol. The mixture was filtered and 7.8 g of methoxyacetonitrile was added dropwise to the filtrate. The mixture was left for 48 hours. The mixture was then cooled to 4° C. Filtration and evaporation of the filtrate give 8.7 g of the title compound.

The following compounds were synthesized from the appropriate nitriles in an analogous manner:
Propionamide oxime
Cyclopropyl carboxamide oxime
Isopropyl carboxamide oxime B.
3-(3-cyclopropyl-1,2,4-oxadiazol-5-yl)-4,5-dihydro-4-methyl-5-oxo-6-chloro-imidazo(1,5-a)quinazoline and 3-(3-cyclopropyl-1,2,4-oxadiazol-5-yl)-4,5-dihydro-4-methyl-5-oxo-6-ethoxy-imidazo(1,5-a)quinazoline 50 mg of sodium was dissolved in 20 ml of dryethanol containing 3 g of molecular sieves(4Å) and 0.5 g of cyclopropylcarboxamide oxime was added to this mixture and thereupon 0.2 g of ethyl 4,5-dihydro-4-methyl-5-oxo-6-chloro-imidazo(1,5-a)quinoxaline-3-carboxylate. The resulting mixture was refluxed for 2 hours. The product was isolated by filtration, reduction of the volume of the reaction mixture in vacuo followed by addition of icewater and filtration. T.L.C. showed content of two compounds, which were isolated by chromatography on silica gel with ethyl acetate.

Yield: 5.7 mg of 6-chloro compound M.p. 200°–205° C. 5.Omg of 6-ethoxy compound M.p. 238°–240° C.

3-(3-isopropyl-1,2,4-oxadiazol-5-yl)-4,5-dihydro-4-methyl-5-oxo-6-chloro-imidazo(1,5-a)quinazoline, M.p.208.7°–209.3° C. was prepared in exactly the same manner from isopropyl carboxamide oxime.

EXAMPLE 4

6-cyano-3-(5-cyclopropyl-1,2,4-oxadiazol-3-yl)-4,5-dihydro-4-methyl-5-oxo-imidazo(1,5-a)quinazoline.

To 140 mg 6-bromo-3-(5-cyclopropyl-1,2,4-oxadiazol-3-yl)4,5---dihydro-4-methyl-5-oxo-imidazo(1,5-a)quinazoline in 5 ml dimethyl formamide (DMF) 40 mg cuprous cyanide was added. Thereafter further 5 ml DMF was added and the resulting mixture was heated to 130°–150° C. for 60 minutes with stirring. To this mixture 110 mg sodium cyanide in 5 ml water was added and thereafter further 30 ml water. The resulting mixture was extracted with 30 ml ethyl acetate and thereafter four times with 20 ml ethyl acetate. The combined organic phase was washed with water and dried with calcium chloride. Evaporation in vacuo gave 24 mg of the title compound. M.p. 115°–125° C.

EXAMPLE 5

A. 1,2,3,4-tetrahydro-3-ethyl-2,4-dioxo-quinazoline

To a mixture of 12.23 g of ethylamine hydrochloride, 35 ml 4M sodium hydroxide and 175 ml methylene chloride was added 16.3 g isatoic anhydride. This mixture was stirred for 4 hours and the aqueous phase was made basic with 4 M sodium hydroxide. The organic phase was evaporated in vacuo. The residue was dissolved in 300 ml of tetrahydrofuran (THF) and 75 ml phosgene solution (20% in toluene) was added. The resulting mixture was stirred at 80° C. for two hours. The precipitate was filtered off and the mother liquor was evaporated leaving 5.2 g of the title compound. M.p. 189.8°–189.9° C.

In exactly the same manner the following compounds were prepared:

1,2,3,4-tetrahydro-3-cyclopropyl-2,4-dioxo-5-chloro-quinazoline, M.p. 284.8°–285.0° C., from cyclopropylamine and 6-chloroisatoic anhydride.

1,2,3,4-tetrahydro-3-ethyl-2,4-dioxo-5-chloro-quinazoline, M.p. 267.2°–267.5° C., from ethylamine and 6-chloroisatoic anhydride.

B.
3-(5-cyclopropyl-1,2,4-oxadiazol-3-yl)-4,5-dihydro-4-ethyl-5-oxo-imidazo(1,5-a)quinazoline To a mixture of 1.9 g 1,2,3,4-tetrahydro-3-ethyl-2,4-dioxyquinazoline and 450 mg sodium hydride in 50 ml of dry dimethyl formamide (DMF)cooled to −20° C. and under an atmosphere of nitrogen was added 1.1 ml chlorodiethylphosphate. To this mixture was added a −30° C. cold solution of 1.3 g K-tbutoxide and 2.2 g 3-isocyanomethyl-5-cyclopropyl-1,2,4-oxadiazole in 20 ml of dry DMF. The resulting mixture was stirred for 20 minutes whereafter 1 ml acetic acid/50 ml water/20 ml diethyl ether was added which caused the product to precipitate. Yield 0.6 g. M.p. 180°–181° C.

The following compounds were prepared in exactly the same manner:

Ethyl 4,5-dihydro-4-ethyl-5-oxo-6-chloro-imidazo(1,5-a)quinazoline-3-carboxylate, M.p. 226.4°–226.6° C., by reaction between 3-ethyl-1,2,3,4-tetrahydro-2,4-dioxo-5-chloro-quinazoline and ethyl isocyanoacetate.

Ethyl 4,5-dihydro-4-cyclopropyl-5-oxo-6-chloro-imidazo(1,5-a)quinazoline-3-carboxylate, M.p. 207.0°–210.5° C., by reaction between 3-cyclopropyl-1,2,3,4-tetrahydro-2,4-dioxo-5-chloroquinazoline and ethyl isocyanoacetate.

3-(5-cyclopropyl-1,2,4-oxadiazol-3-yl-4,5-dihydro-4-ethyl5-oxo-6-chloro-imidazo(1,5-a)quinazoline. M.p. 217.7°–218.1° C. by reaction between 3-ethyl-5-chloro-1,2,3,4-tetrahydro-2,4-dioxo-quinazoline and 5-cyclopropyl-3-isocyanomethyl-1,2,4-oxadiazole.

3-(5-cyclopropyl-1,2,4-oxadiazol-3-yl-4,5-dihydro-4-cyclo-propyl-5-oxo-6-chloro-imidazo(1,5-a)quinazoline. M.p. 232°–235° C. by reaction between 3-cyclopropyl -5-chloro-1,2,3,4-tetrahydro-2,4-dioxo-quinazoline and 5-cyclopropyl-3-isocyanomethyl-1,2,4-oxadiazole.

EXAMPLE 6

Methyl 4,5-dihydro-4-methyl-5-oxo-6-chloro-imidazo(1,5-a)-quinoxaline-3-carboxylate 1 g of 4,5-dihydro-4-methyl-5-oxo-6-chloro-imidazo(1,5-a)quinoxaline-3-carboximidazolide ( conventionally prepared by reacting the free acid with N,N-carbonyldiimidazole) was refluxed in 20 ml of methanol at 60° C. for 17 hours. The reaction mixture was eveporated in vacuo and the product was crystallized from water. Yield 0.82 g of title compound. M.p. 210°-220° C.

Isopropyl 4,5-dihydro-4-methyl-5-oxo-6-chloro-imidazo(1,5-a)-quinoxaline-3-carboxylate, M.p. 215.7°-219.5° C. was prepared in exactly the same manner by refluxing in isopropanol.

Cyclopropylmethyl 4,5-dihydro-4-methyl-5-oxo-6-chloro-imidazo(1,5-a)quinoxaline-3-carboxylate, M.p. 214.2°-214.3° C. was prepared in exactly the same manner by refluxing in cyclopropylmethanol.

In conclusion, from the foregoing, it is apparent that present invention provides novel neurologically-effective benzodiazepine receptor binding imidazoquinazoline compounds and salts thereof, having advantageous and unpredictable properties, as well as novel pharmaceutical compositions thereof and method of treating therewith, all possessed of the foregoing more specifically-enumerated characteristics and advantages.

It is to be understood that the invention is not to be limited to the exact details of operation, or to the exact compositions, methods, procedures, or embodiments shown and described, as obvious modifications and equivalents will be apparent to one skilled in the art, and the invention is therefore to be limited only by the full scope of the appended claims.

We claim:

1. A compound having the formula $CN-CH_2-Z$ wherein Z is

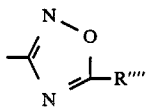

wherein
R'''' is $C_{1-6}$-alkyl or $C_{3-7}$-cycloalkyl,

2. Compound of claim 1 which is 5-methyl-3-isocyanomethyl-1,2,4-oxadiazole.

3. Compound of claim 1 which is 5-Cyclopropyl-3-isocyanomethyl-1,2,4-oxadiazole.

* * * * *

UNITED STATES PATENT AND TRADEMARK OFFICE
CERTIFICATE OF CORRECTION

PATENT NO. : 4,780,539　　　　　　　　　　　　　　Page 1 of 2

DATED : October 25, 1988

INVENTOR(S) : Frank Watjen and Mogens Engelstoft

It is certified that error appears in the above-identified patent and that said Letters Patent is hereby corrected as shown below:

Col. 2, line 1; "reoeptors" should read -- receptors --
Col. 2, line 3; "follow:" should read -- follows: --
Col. 2, line 27; "µphysiological" should read -- µl physiological --
Col. 2, line 30; before "7.1," insert -- pH --
Col. 3, line 37; in Table 1, column 4, 5th formula in that column; "$COC_2H_5$" should read -- $CO_2C_2H_5$ --

Col. 6, line 24; "to hundred" should read -- to one hundred --
Col. 6, line 43; "pharmaceuticol" should read -- pharmaceutical --
Col. 7, line 10; "amelioration." should read -- amelioration, --
Col. 8, line 61; separate the word ending with "methyl" and the word beginning with "1,2,4-" with a dash -- - --
Col. 8, line 65; "HO" should read -- $H_2O$ --
Col. 9, line 4; "cm-." should read -- $cm^{-1}$. --
Col. 9, line 9; "-isocyaomethyl-" should read -- -isocyanomethyl- --

UNITED STATES PATENT AND TRADEMARK OFFICE
CERTIFICATE OF CORRECTION

PATENT NO. : 4,780,539

DATED : October 25, 1988

INVENTOR(S) : Frank Wätjen and Mogens Engelstoft

It is certified that error appears in the above-identified patent and that said Letters Patent is hereby corrected as shown below:

Col. 9, line 46; separate the word ending with "methyl" and the word beginning with "1,2,4-" with a dash -- - --
Col. 10, line 35; "-3methyl-" should read
-- -3-isocyano-methyl- --
Col. 10, line 47; "methyl5-oxo-" should read -- methyl-5-oxo- --
Col. 10, line 52; "imidazo(1.5-a)-" should read
-- imidazo(1,5-a)- --
Col. 10, line 53; "by 3-" should read -- by reaction between 3- --
Col. 10, line 56; "methyl5-oxo-" should read
-- methyl-5-oxo- --
Col. 10, line 67; "methyl5-oxo-" should read -- methyl-5-oxo- --
Col. 11, line 37; "dryethanol" should read -- dry ethanol --
Col. 11, line 59; "-yl)4,5--" should read -- -yl)4,5- --
Col. 12, line 32; "ethyl-5-" should read -- -ethyl-5- --
Col. 12, line 37; "1.1 ml" should read -- 1.7 ml --
Col. 12, line 59; "ethyl5-oxo-" should read
-- ethyl-5-oxo- --
Col. 13, line 12; "eveporated" should read -- evaporated --
Col. 14, line 22; "cycloalkyl," should read -- cycloalkyl. --

Col. 9, lines 4 and 57; in both instances "absorbtion" should read
-- absorption --

Signed and Sealed this

Tenth Day of July, 1990

*Attest:*

HARRY F. MANBECK, JR.

*Attesting Officer*     Commissioner of Patents and Trademarks

UNITED STATES PATENT AND TRADEMARK OFFICE
CERTIFICATE OF CORRECTION

PATENT NO. : 4,780,539

DATED : October 25, 1988

INVENTOR(S) : Frank Watjen, et al

It is certified that error appears in the above-identified patent and that said Letters Patent is hereby corrected as shown below:

Title Page, [30] Foreign Application Priority Data; insert
  before the first line the following:
  -- May 17, 1985 [DK]   Denmark ........ 2204/85
     Aug. 12, 1985 [DK]  Denmark ........ 3659/85 --
  ( See Continuation-in-part Declaration dated May 26, 1988, filed 6/9/88)
Title Page, [56] References Cited, U.S. PATENT DOCUMENTS, before
  the first line, insert
  -- 3,600,390  8/1971  Sherlock ....  544/250 --
  (See Petition and PTO 892 with references filed January 12, 1988)
Title Page, [56] References Cited, after the foreign patent
  document cited (0150040) --- insert after that line the following
  --          OTHER PUBLICATIONS
          Singh, et al. Chemical Abstracts, Vol. 70:87715d(1969)
          Talukdar, et al. Chemical Abstracts, Vol. 94:65615q
              (1981) --

Signed and Sealed this

Twelfth Day of February, 1991

Attest:

HARRY F. MANBECK, JR.

*Attesting Officer*     *Commissioner of Patents and Trademarks*